US010524748B2

(12) United States Patent
Freesmeyer (10) Patent No.: US 10,524,748 B2
(45) Date of Patent: Jan. 7, 2020

(54) METHOD FOR DETERMINING THE LOCATIONS OF ORIGIN OF RADIATION SIGNALS IN A MEASUREMENT ZONE, AND MEASURING DEVICE FOR SIMULTANEOUSLY DETECTING RADIATION EVENTS OF DECAYING RADIONUCLIDES IN THE MEASUREMENT ZONE (71) Applicant: Universitaetsklinikum Jena, Jena (DE)

(72) Inventor: Martin Freesmeyer, Jena (DE)

(73) Assignee: Universitaetsklinikum Jena, Jena (DE)

( * ) Notice: Subject to any disclaimer, the term of this patent is extended or adjusted under 35 U.S.C. 154(b) by 610 days.

(21) Appl. No.: 15/317,613

(22) PCT Filed: Jun. 11, 2015

(86) PCT No.: PCT/DE2015/100233
§ 371 (c)(1),
(2) Date: Dec. 9, 2016

(87) PCT Pub. No.: WO2015/188810
PCT Pub. Date: Dec. 17, 2015

(65) Prior Publication Data
US 2017/0119327 A1    May 4, 2017

(30) Foreign Application Priority Data
Jun. 11, 2014    (DE) .................. 10 2014 108 178

(51) Int. Cl.
*A61B 6/00*    (2006.01)
*A61B 8/00*    (2006.01)
*A61B 8/08*    (2006.01)

(52) U.S. Cl.
CPC .......... *A61B 6/4417* (2013.01); *A61B 6/4233* (2013.01); *A61B 6/4241* (2013.01);
(Continued)

(58) Field of Classification Search
CPC ..... A61B 6/4417; A61B 6/4233; A61B 6/463; A61B 8/4444; A61B 8/463; A61B 8/5261;
(Continued)

(56) References Cited

U.S. PATENT DOCUMENTS 3,890,959 A    6/1975 Youdin et al.
6,429,431 B1    8/2002 Wilk
(Continued)

FOREIGN PATENT DOCUMENTS

DE    10 2012 111 386 A1    5/2014
EP    1 284 655 B1    12/2005

OTHER PUBLICATIONS

Panin, Vladimir, Y., et al.; "Fully 3-D PET Reconstruction with System Matrix Derived From Point Source Measurements"; *IEEE Transaction on Medical Imaging* 2006; 25(7):907-921.

*Primary Examiner* — David P Porta
*Assistant Examiner* — Gisselle Gutierrez
(74) *Attorney, Agent, or Firm* — Duane Morris LLP (57) ABSTRACT A method for determining the locations of origin of radiation signals in a measurement zone in which radiation signals are detected from the measurement zone by means of a quantity of radiation detectors at a measurement time, and measurement values associated with the measurement time are provided. The determination of the locations of origin is carried out taking into account the measurement values of all of the radiation detectors and of the known positional relationships of the radiation detectors relative to one another using a reference dataset. The measuring device of the invention, for the simultaneous detection of radiation events of decaying radionuclides in the measurement zone has a quantity of radiation detectors provided in a measuring head. An ultrasound probe may be arranged in the measuring head. Detection, determination and imaging of a two-dimen- (Continued)

sional intensity distribution of radiation signals of a radionuclide is possible in the entire measurement zone.

13 Claims, 5 Drawing Sheets

(52) U.S. Cl.
CPC ............ *A61B 6/4258* (2013.01); *A61B 6/463* (2013.01); *A61B 6/5205* (2013.01); *A61B 6/5247* (2013.01); *A61B 8/4416* (2013.01); *A61B 8/4444* (2013.01); *A61B 8/463* (2013.01); *A61B 8/5261* (2013.01)

(58) Field of Classification Search
CPC ... A61B 6/5247; A61B 6/4241; A61B 6/4258; A61B 6/5205; A61B 8/4416; A61B 8/5246; A61B 6/4266; A61B 8/085; G01T 1/1603; G01T 1/161
USPC ...................................................... 250/336.1
See application file for complete search history.

(56) References Cited

U.S. PATENT DOCUMENTS

| | | |
|---|---|---|
| 6,512,943 B1 | 1/2003 | Kelcz |
| 7,094,203 B2 | 8/2006 | Inoue et al. |
| 2005/0218331 A1 | 10/2005 | Blevis et al. |
| 2006/0237652 A1 | 10/2006 | Kimchy et al. |
| 2009/0123048 A1 | 5/2009 | Leroux et al. |
| 2012/0032086 A1 | 2/2012 | Daghighian |
| 2013/0172739 A1 | 7/2013 | Paladini |
| 2015/0305700 A1 | 10/2015 | Wendler et al. |

METHOD FOR DETERMINING THE LOCATIONS OF ORIGIN OF RADIATION SIGNALS IN A MEASUREMENT ZONE, AND MEASURING DEVICE FOR SIMULTANEOUSLY DETECTING RADIATION EVENTS OF DECAYING RADIONUCLIDES IN THE MEASUREMENT ZONE

RELATED APPLICATIONS

The present application is a U.S. National Stage application of International PCT Application No. PCT/DE2015/100233 filed on Jun. 11, 2015 which claims priority benefit of German Application No. DE 10 2014 108 178.1 filed on Jun. 11, 2014, the contents of each are incorporated by reference in their entirety.

FIELD OF THE INVENTION

The invention relates to the field of multimodal imaging, also known as hybrid imaging. It is directed particularly to a method and device for determining the location of origin of radiation signals in a measurement zone as is known generically from US 2013/0172739 A1.

BACKGROUND OF THE INVENTION

Methods in which structures that are located at a depth (Z direction) below the surface of an examined object are imaged by means of ultrasound signals in a measurement zone are applied for a range of applications, for example, in materials testing and product testing and in medicine. A typical example of this is sonography. This is, by nature, a method for section imaging (ultrasound tomography). A section image of the sonogram with conventional ultrasound probes shows a sectional view of an object under examination, for example, in a material or in a bodily tissue. In doing so, differences in the acoustical (reflection) characteristics in the interior of the object under examination (ultrasound signals) are visualized. In the two-dimensional section image generated in this way, a first dimension extends along a crystal array of the ultrasound head (X direction). The second dimension reflects the distribution of the acoustical characteristics in depth (Z direction). Therefore, the measurement zone examined in this way preferably extends in an X-Z plane and has only a slight thickness in Y direction.

In contrast, in methods based on the detection of radiation signals of radionuclides, two-dimensional images are acquired through which a two-dimensional distribution of radiation signals and their intensities is imaged in an X-Y plane. It is not possible to directly correlate the two-dimensional distribution with a depth localization of locations of origin of the radiation signals in an individual image.

Conventional gamma probes deliver information only as number and/or acoustical signal (whistle, clicking sound) so that no information about the depth location of a storage lesion is obtained. These probes use an individual gamma detector and a passive metal collimator of high density to define the visual field of the detector and to suppress background radiation from the environment in that this background radiation does not reach the detector and is not detected by it. With high power, the collimators are large and heavy.

Apparatus is known in which an ultrasound probe and at least one radiation detector are arranged in proximity to one another or in a common measuring head.

A solution of this kind is known from U.S. Pat. No. 7,094,203 B2. In a housing, a collimator is arranged upstream of a quantity of radiation detectors (array), and a detection zone of the radiation detectors is directed and limited through the action of the collimator. Directly adjacent to the housing, an ultrasound probe is arranged in a common measuring head. Ultrasound signals are detected in a common measurement zone by the ultrasound probe in an X-Z plane. The array of radiation detectors is swivelably arranged so that a measurement zone of the array can be directed through the measurement zone of the ultrasound probe. By means of a swiveling movement of the array, a point of intersection of the two measurement zones can be displaced as a focal plane along the measurement zone of the ultrasound probe and various measurement positions of the radiation detectors can be adjusted with respect to the common measurement zone. The information about depth localization of locations of origin can be obtained by reconstructing the individual focal planes.

A similar method is described in EP 1 284 655 B1. In this case, a quantity of radiation detectors is arranged so as to be directed at various angles into a measurement zone, and the detection zones of the radiation detectors intersect in a focus line in the measurement zone. For the alignment of the detection zones of the radiation detectors which is critical for this purpose, a collimator is arranged upstream of each radiation detector. The respective angles of the radiation detectors are known. By making use of the knowledge of the respective currently adjusted angles, the position of a current focus line can be determined. If the focus line is guided through the measurement zone and, in so doing, the detected radiation signals are stored such that they are associated with the respective focus line, an imaging of the radionuclide distribution, i.e., the locations of origin, can be reconstructed. In addition, an ultrasound image of the measurement zone is captured. The data from the ultrasound tomogram and the reconstruction of the distribution of the locations of origin in the common measurement zone can subsequently be imaged in a hybrid image.

A measuring head in which an ultrasound probe is arranged next to or in an array of radiation detectors is known from US2013/0172739A1. Detection of ultrasound signals and radiation signals is only possible in a directed manner. The three-dimensional distribution of the locations of origin is only possible through detection of corresponding measurement values from different measurement positions of the measuring head and through reconstruction of the measurement values detected at the various measurement positions.

All of the solutions of the prior art require a reconstruction of data in order to image a distribution of the locations of origin and ultrasound images based on radiation signals and ultrasound signals. A definitive spatial association of increased nuclide-storing findings with the sonogram is only possible at high computational expenditure and with a very high risk and unpredictability of spatial offsets caused by the calculation algorithms. Therefore, it would be desirable to provide an integrated probe for generating anatomically correctly matching section images (identical imaging planes) simultaneously as far as possible from tissue echogenicity (ultrasound signals) and radionuclide distribution. There is no satisfactory state-of-the-art solution at the present time.

SUMMARY OF THE INVENTION

It is an object of the invention to suggest a possibility for detecting radiation events of decaying radionuclides in a measurement zone by which a simplified handling and an improved spatial resolution of radiation signals is achieved.

This object is met through the subject matter of the independent claims. Advantageous embodiments are indicated in the dependent claims.

The object is met in a method for determining the locations of origin of radiation signals in a measurement zone in which a quantity n=2, 3, . . . , i of radiation detectors for receiving radiation signals from the measurement zone and for providing measurement values based on received radiation signals are arranged in a known relative spatial arrangement relative to one another, wherein each of the radiation detectors has a different geometric efficiency with respect to the detection of measurement values of radiation signals which originate from different locations of origin of the common measurement zone. By means of the quantity of radiation detectors, radiation signals are detected from the measurement zone at a measurement time and, based on the detected radiation signals, measurement values are provided so as to be associated with the measurement time. The determination of the locations of origin of the radiation signals is carried out taking into account the measurement values of all of the radiation detectors and of the known positional relationships of the radiation detectors relative to one another. The determination of the locations of origin is further carried out using a reference dataset, and the reference dataset is made up of a quantity of partial reference datasets, and every partial reference dataset is formed by specific data of a location of origin in each instance, and the specific data are formed by relationships of measurement values of the radiation detectors with respect to one another.

Specific data are preferably data which are associated with a location of origin (location-specific) and which are obtained by defining a three-dimensional measurement zone in which each spatial point can be uniquely described by coordinates of a suitable coordinate system, for example, a Cartesian coordinate system or a polar coordinate system. A spatial point of this type is a location. If a radionuclide decays at a spatial point of this kind and a radiation signal emanates from this spatial point, then this spatial point is a location of origin within the meaning of this description. The detected radiation signal causes a signal value in each radiation detector, particularly a signal value of the intensity of the detected radiation signal. An individual signal value is detected by each radiation detector as a measurement value and is stored. The individual measurement values are related to one another, and the partial reference datasets are formed and are stored so as to be associated with one of the locations of origin in each instance. In addition, the signal values can be saved in the partial reference datasets so as to have data available about the intensities of the detected radiation signals and so that they can be imaged. The intensities are preferably accentuated by suitable colored and/or other graphic emphases such as shading, borders, gray value depictions, blinking depictions, etc. in an imaging of the locations of origin.

The above considerations are based on an idealized state. In view of the fact that a radionuclide actually has a size in excess of a point, and a source of a radiation signal can hardly be reduced to a spatial point by measurement technology, a location of origin in this description also means a three-dimensional region from which the radiation signal emanates.

A measurement zone is a section of a layer extending in an X-Z plane of a Cartesian coordinate system. The thickness of the layer in Y direction is 1 mm, 3 mm or 5 mm, for example.

Detection and determination of a two-dimensional intensity distribution of the detected radiation signals of the radionuclide is advantageously made possible in the entire measurement zone by means of the method according to the invention. Therefore, based on the detected radiation signals and the intensities thereof, the two-dimensional distribution of the radionuclide in the measurement zone is also derivable. For each spatial point in the measurement zone, the intensity of the radiation signals (radioactivity content) can be determined and associated in each instance with a two-dimensional position in the measurement zone. Positions and intensities can be displayed in an image matrix. Different intensities are preferably imaged in a color-coded or grayscale-coded manner.

By means of the method according to the invention, it is also possible to define a plurality of measurement zones located next to one another and to generate a three-dimensional distribution of the locations of origin and their respective intensities based on the provided measurement values.

Since individual technical component elements such as radiation detectors are not absolutely identical with respect to characteristic curves, it is advantageous when the measurement values provided by each radiation detector are calibrated if required. Accordingly, differences in the individual efficiency of the detection of radiation signals of the radiation detectors can be calibrated in that every measurement value is calculated, for example, multiplied, by a calibration factor. The calibrated measurement values are used for determining the reference dataset.

Further, it may come about that signal values are detected and measurement values are provided by the radiation detectors although no radiation signals at all emanate from the measurement zone. This effect can be based, for example, on a detection of radiation signals from outside the measurement zone and on physical and chemical processes within the radiation detectors. Such data, known as background measurement values, are advantageously also determined and taken into account during preparation of the reference dataset in that the measurement values are corrected with reference to the background measurement values.

It is further possible that the calibration factors as well as the background measurement values are adapted, or must be adapted, over the duration of the implementation of the method and/or over the lifetime of a radiation detector (long-term drift).

The individual adaptations and corrections mentioned above can also be carried out and/or taken into account when providing the measurement values.

Measurement values which have been signally prepared are also considered as measurement values which are provided by the radiation detectors. Accordingly, detected radiation signals can be detected as signal values and subsequently filtered, transformed and/or smoothed before they are provided as measurement values.

It is further very advantageous when a measurement value is provided, for example, as an average of a quantity of detected radiation signals rather than a measurement value which is based on an individually detected radiation signal and on the signal value resulting therefrom. Arithmetic averages, weighted averages, sliding averages or geometric averages and modifications thereof can be used as average values. Since the formation of averages demands that there be a quantity of measurement values of different measurement times, a time period during which a quantity of measurements is carried out is also to be understood under the term "measurement time" in addition to an individual time at which a measurement is carried out.

A reference dataset is provided, for example, in that a known amount of one or more radionuclides is placed in a measurement zone at a known location of origin and the measurement values which are provided on the basis of the detected radiation signals for each radiation detector are saved so as to be associated with the location of origin and with a measurement time. The radiation detectors are arranged in a known relative position with respect to the measurement zone and oriented (measurement position) to the latter. Subsequently, the measurement values of the radiation detectors provided are related according to predetermined rules. Such relationships are mathematical relationships, for example, quotients, subtractions, additions, products and combinations thereof. These relationships and the respective results thereof are stored as partial reference datasets so as to be associated with the respective location of origin. Additional data, for example, the type and amount of radionuclides used and further data on the conditions during the generation of the reference dataset can be associated with the partial reference datasets and stored for later recall.

Subsequently, the procedure described above is repeated for further locations of origin until a reference dataset with a desired spatial resolution of the locations of origin is generated.

During the generation of the reference dataset, calibration factors and background measurement values can be determined in addition. Long-term drifts can be determined or estimated by generating reference datasets repeatedly at different times. Reference datasets which have been prepared at different times can be compared with one another, and determined systematic deviations of the measurement values can be used for detecting and correcting long-term drifts.

It is also possible for a computer-assisted simulation to be carried out for some or all locations of origin and for the provided measurement values to be determined based on the simulation. Further, it is possible that radiation signals are actually detected for a determined selection of locations of origin and, for example, calibration factors and background measurement values are determined. Based on these selected locations of origin, calibration factors and/or background measurement values can be extrapolated for the reference dataset.

The method according to the invention advantageously makes it possible to determine locations of origin of radiation signals without having to change a measurement position of the radiation detectors.

In further embodiments of the method according to the invention, the locations of origin of the detected radiation signals determined at a measurement time can be provided as imaging data for a graphic display of the measurement zone with the locations of origin. Graphic displays can be carried out, for example, on a monitor, as a projection and/or as printed reproduction of the measurement zone and locations of origin.

In an advantageous further development of the method according to the invention, it is possible for ultrasound signals to be detected additionally from the measurement zone at the measurement time and provided as ultrasound measurement values associated with the measurement time for a graphic depiction of the measurement zone. The locations of origin of the radiation signals and the ultrasound measurement values are displayed in a graphic display simultaneously and correctly with respect to location and position. These data are preferably imaged in a hybrid image.

Accordingly, it is possible by means of the above-mentioned further development of the method according to the invention to generate an image of the intensity distribution of the detected radiation signals (image matrix) in the common measurement zone, i.e., in this case in the X-Z plane of the ultrasound.

A measurement zone is preferably defined by a section of a detection zone of the radiation detectors in which an efficient and precise detection and localization of the locations of origin is possible. A detection of the locations of origin is also made possible in Z direction by the configuration of the method according to the invention. Since a detection of ultrasound signals is also carried out in Z direction, it is also possible to determine and detect locations of origin of radiation signals as well as ultrasound signals and to (collectively) image them simultaneously in a measurement zone having an extension preferably in a X-Z plane.

By configuring the method according to the invention in this way, a very advantageous combination of two measuring methods is achieved with the simultaneous display of the locations of origin and of the ultrasound measurement values. If necessary, the measurement values of the radiation signals and intensities of the signal values can be displayed in a suitable manner in addition. Accordingly, they can be imaged as numerical values and in the form of a color code, for example, color-coded, or as gray value.

In contrast to the methods known from the prior art, it is not necessary with the method according to the invention to detect the radiation measurement values and the ultrasound measurement values from different measurement positions in order to generate an image. Images are possible in real time, and images with slight time lags due to computation are nevertheless validly provided in real time. In addition, it is very favorable that no reconstruction of the images is required by the method according to the invention. In an advantageous manner, this reduces or completely prevents an erroneous spatial offsetting of the imaged radiation measurement values and, as the case may be, the ultrasound measurement values relative to one another, which frequently occurs due to simplifications in the calculation algorithms used for the reconstruction.

Further, it is possible for the radiation detectors to be arranged without a collimator upstream of the radiation detectors on the reception side. Such an embodiment of the method makes it possible to use lighter apparatus and to avoid limiting the reception zone of the radiation detectors.

The method according to the invention can be utilized to determine locations of origin of radiation signals and, accordingly, to determine the spatial distribution of radionuclides in a measurement zone. Applications can be in the field of metrology, materials and quality control and medicine, for example.

Particularly when the method according to the invention is combined with the simultaneous detection and imaging of ultrasound measurement values, the possibility of being able to simultaneously detect and image radiation measurement values and ultrasound measurement values without having to detect data from multiple measurement positions is advantageously made available for medical applications.

The above-stated object is further met with a measuring device for simultaneously detecting radiation events of decaying radionuclides in a measurement zone in which a quantity of radiation detectors is provided in a measuring head of the measuring device in a known spatial arrangement relative to one another, and the radiation detectors serve to receive radiation signals from the measurement zone and to provide measurement values based on received radiation signals. Each of the radiation detectors has a geometric efficiency with respect to the detection of measurement values of radiation signals which originate from different locations of origin of the common measurement zone. The measuring device further has an evaluating unit for evaluating the radiation signals and for determining the locations of origin of each of the radiation signals. The evaluating unit is configured in such a way that the locations of origin of the detected radiation signals can be determined from a quantity of measurement values which were detected at only one, measurement position of the measuring head and which are compared with data of a reference dataset. The reference dataset is made up of a quantity of partial reference datasets. Each partial reference dataset is formed by specific data of a location of origin in each instance.

The quantity n of radiation detectors is at least two, which is expressed hereinafter as n=2, 3, . . . , i.

The radiation detectors are advantageously detectors by which an intensity of the detected radiation signals can be provided as measurement value. Detectors of this type are, for example, semiconductor detectors such as CdZnTe detectors or $HgJ_2$ detectors. In these detectors, a photo effect is triggered by a radiation (radiation signal), for example, gamma radiation, impinging on the semiconductor material, the intensity of this photo effect being proportional to the intensity of the radiation signal. An intensity measurement is carried out by measuring a current flow (current pulse) initiated by the photo effect.

Other suitable detectors are scintillation detectors, for example, $Bi_4Ge_3O_{12}$ detectors, $Lu_2SiO_5$:Ce detectors, $Lu_{0.8}Y_{0.2}AlO_3$:Ce detectors, $Gd_2SiO_5$:Ce detectors CsJ:Tl detectors or NaJ:Ti detectors. These materials have a high light yield and short decay times. In scintillation detectors, an ionization caused by a detected radiation signal is transformed into flashes which are detected by a suitable photodiode or a photo multiplier. The brightness of the detected flashes is proportional to the intensity of the radiation signal.

In an advantageous construction of the measuring device according to the invention, the evaluating unit is configured in such a way that the determination of the location of origin of each radiation signal is carried out using the reference dataset, wherein the specific data of each partial reference dataset are formed by relationships of measurement values (see above) of the radiation detectors relative to one another.

In a further construction, an ultrasound probe can be additionally arranged in the measuring head for transmitting and receiving ultrasound signals from the measurement zone. A known ultrasound head in which an array of radiation detectors is integrated may be used as measuring head. An array is an arrangement of at least two radiation detectors which are arranged in a fixed position with respect to one another.

A construction of the measuring device according to the invention that is simpler because it is lightweight and is realized with fewer component parts consists in that the measuring device is constructed as a measuring device without a collimator. This is advantageous because of the quantity of radiation detectors and the configuration of the evaluating unit. A collimation of the signals reaching the measuring head from the measurement zone, particularly radiation signals, can be omitted because the configuration, according to the invention, of the evaluating unit in cooperation with the known relative spatial arrangement of the radiation detectors relative to one another allows a sufficiently precise determination of the locations of origin.

Accordingly, the precision with which locations of origin are determined in advantageous constructions of the device according to the invention is less than 5 mm to 10 mm.

In a construction of the measuring device that is very advantageous because it is meaningful for practical application, the measuring head is a portable device which can be held and guided in one hand by the user. In a preferred construction, the measuring device corresponds in shape and dimensioning to an ultrasound probe such as is known from the art and as is used particularly in the field of medicine for ultrasound examinations of soft tissue.

The radiation detectors can be provided in different arrangements. In one arrangement of the measuring device according to the invention, the radiation detectors are arranged in at least one array.

In further arrangements, the radiation detectors can be arranged around the at least one ultrasound probe so that the latter is arranged in an array of radiation detectors.

In a further construction, the at least one ultrasound probe can also be arranged next to an array of radiation detectors. Further, it is possible that the array of radiation detectors is arranged behind the at least one ultrasound probe so that the radiation signals pass through regions of the ultrasound probe before they can be detected by the radiation detectors. This construction allows a particularly compact constructional form.

BRIEF DESCRIPTION OF THE DRAWINGS

The invention will be described more fully in the following with reference to embodiment examples and illustrations. The drawings show.

DESCRIPTION OF THE EMBODIMENTS

The embodiment examples are shown schematically and are not shown true-to-scale. Identical reference numerals always designate identical technical features unless otherwise expressly stated.

Figure 1:
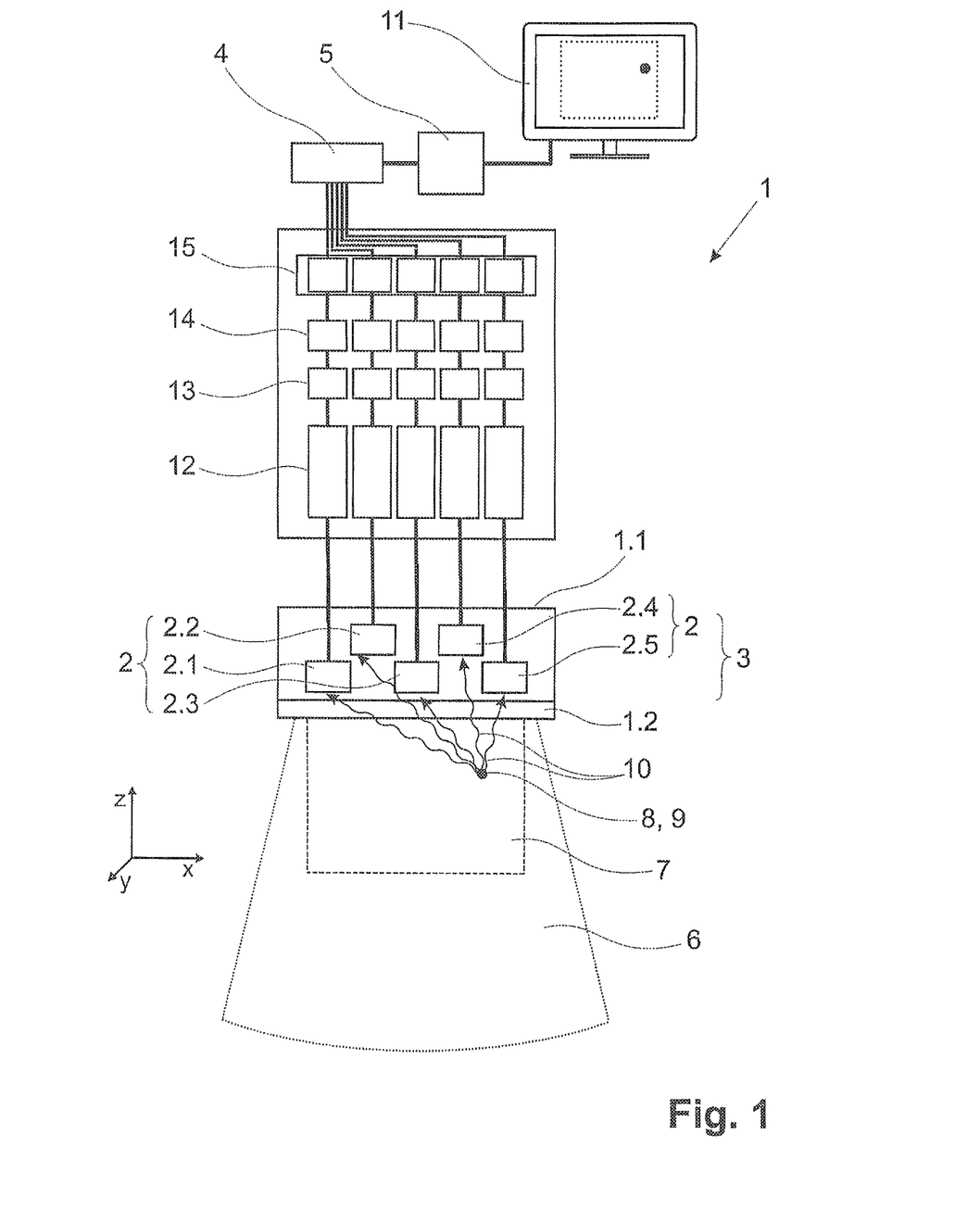
FIG. 1 is an embodiment example of a measuring device according to the invention with an array of radiation detectors in a measuring head.

An embodiment example of a measuring device 1 according to the invention is described with reference to FIGS. 1 and 2. The measuring device 1 which is constructed as a real-time handheld emission spot allocator (rthESA) comprises three main components: an array 3 of radiation detectors 2, an electronic evaluating unit 4 and a computer-assisted workstation 5.

The array 3 is arranged in a housing of a measuring head 1.1 and, in the embodiment example, comprises a first radiation detector 2.1, a second radiation detector 2.2, a third radiation detector 2.3, a fourth radiation detector 2.4 and a fifth radiation detector 2.5. The first to fifth radiation detectors 2.1 to 2.5 are CdZnTe semiconductor detectors with an edge length of 4.8 mm which are arranged alternatingly in an X-Z plane perpendicular to an entrance window 1.2 of the measuring head 1.1. The first, third and fifth radiation detectors 2.1, 2.3 and 2.5 are arranged directly at the entrance window 1.2 of the measuring head 1.1 (front detectors), while the second and fourth radiation detectors 2.2 and 2.4 are arranged farther away from the entrance window 1.2 (rear detectors). The first radiation detector 2.1 and third radiation detector 2.3 and the third radiation detector 2.3 and fifth radiation detector 2.5 are arranged relative to one another with a gap therebetween in each instance, the second radiation detector 2.2 and fourth radiation detector 2.4, respectively, are arranged corresponding to these gaps. The X-Z plane in which the first to fifth radiation detectors 2.1 to 2.5 of the array 3 are arranged extends in direction of the X axis and in direction of the Z axis of a Cartesian coordinate system associated with the measuring device 1.

Depending on the locations of origin 9 from which a radiation signal 10 (symbolized by curly arrows) of a radionuclide 8 (shown together with the location of origin 9 for the sake of simplicity) is detected by the first to fifth radiation detectors 2.1 to 2.5, the radiation signal 10 in question had to cover a path of varying length to reach the first to fifth radiation detectors 2.1 to 2.5, respectively. The lengths of the paths which were covered inside a medium of the measurement zone 7 also differ. Further, a radiation signal 10 impinges on the first to fifth radiation detectors 2.1 to 2.5 at different angles so that the effect of the radiation signal 10 on the respective first to fifth radiation detectors 2.1 to 2.5, i.e., the geometric efficiency of the respective first to fifth radiation detectors 2.1 to 2.5, differs with respect to the detection of a radiation signal 10 from a determined location of origin 9 and depends on the localization of this location of origin 9.

The CdZnTe semiconductor detectors (response time <80 ns; dead time 20 µs) are very compact, have a high efficiency (approximately 80%) and require no bulky photo multipliers. The radiation detectors 2 are capable of counting 100 to 50,000 events per second (counts per second or cps). The total dead time of the measuring device 1 is 20 µs. In further embodiments of the measuring device 1 according to the invention, other radiation detectors 2 with other technical parameters can be arranged.

The measurable energy spectrum ranges from 100 to 550 keV. The first to fifth radiation detectors 2.1 to 2.5 were operated with a reverse bias and with fivefold preamplifiers 12 (12 V, low voltage). The signals of the first to fifth radiation detectors 2.1 to 2.5 caused by the detected radiation signals 10 in the respective radiation detectors 2 are amplified separately from one another and transmitted. The respective current pulses of the first to fifth radiation detectors 2.1 to 2.5 are converted into a voltage pulse by each preamplifier 12. Since these voltage pulses have a high noise component, modulators 13 with a bandpass filter through which the respective voltage pulse is converted into a signal with Gaussian distribution are arranged downstream. All of the signals are switched off below a threshold of 40 keV by a downstream discriminator 14, respectively, and the signal with a Gaussian distribution is converted into a logic pulse (pulse present: yes/no; I/O) which is counted by a counter card 15, and the count event is stored so as to be associated with a respective measurement time. The counter card 15 is signally connected to an evaluating unit 4 and to a computer-assisted workstation 5. The workstation 5 has a display 11 for graphically showing the locations of origin 9 of the radiation signals 10 and the intensities thereof.

The evaluating unit 4 is configured in such a way that the counting events per second (cps) are detected by it for each of the first to fifth radiation detectors 2.1 to 2.5, and sliding averages of the counting events per second are calculated for each of the first to fifth radiation detectors 2.1 to 2.5 and are stored such that they are associated with a measurement time or a measurement period. The five averages represent the measurement values provided by the first to fifth radiation detectors 2.1 to 2.5. Mathematical relationships are calculated as quotients, of the averages, which quotients are calculated from the variously determined combinations. Among these combinations are quotients of the first radiation detector 2.1, third radiation detector 2.3 and fifth radiation detector 2.5 and of the second radiation detector 2.2 and fourth radiation detector 2.4.

For the determined relationships, a reference dataset of sixty-three locations of origin 9 was determined and stored for later recall for purposes of comparison. The reference dataset contains one partial reference dataset per location of origin 9, this partial reference dataset being formed by the same quotients of combinations of measurement values as was explained above. Based on a comparison of the relationships obtained at a measurement time with the partial reference datasets, the best possible match of the relationships with the partial reference datasets is selected and the location of origin 9 of the detected radiation signal 10 is determined.

Basically, radiation signals 10 from an approximately semicircular detection zone 6 can be detected by the radiation detectors 2. However, reproducible events are obtained only from the smaller region. For this reason, an approximately square measurement zone 7 with an extension in direction of the X axis of about 4 cm and an extension in the direction of the Z axis of around 3 cm is determined. Measurement zone 7 has an extension of about one millimeter in direction of the Y axis. Since the measurement zone 7 starts about 1 cm below the front detectors, the entire measurement depth in direction of the Z axis is about 4 cm. A localization of the location of origin 9 of a detected radiation signal 10 can be determined by the known, mutually offset spatial arrangement of the first to fifth radiation detectors 2.1 to 2.5 in conjunction with a comparison of the relationships, of the measurement values with the partial reference datasets.

The reference dataset with the partial reference datasets is generated based on different systems. A first system is established under normal environmental conditions and atmosphere (air phantom), a second system is established for simulation of soft tissue in water (water phantom) and a third system is established in a sample body 19 (see FIG. 3). The liver of an animal, for example, a cow liver, is used as sample body 10.

The first system and second system (neither of which is shown) are formed by a vertically oriented Plexiglas plate having holes at known positions. A capsule with radionuclides 8 (assumed identical to location of origin 9 for the sake of simplicity) is inserted into one of the holes representing the respective location of origin 9, the radiation signals 10 proceeding from the decaying radionuclides 8 are detected and counted and are stored in first to fifth radiation detectors 2.1 to 2.5, respectively, such that they are associated with a measurement time. The detection is carried out from a measurement position of the measuring head 1.1. Sliding averages are calculated for the stored data, and the fixed mathematical relationships are formed from these sliding averages. The specific data determined in this way are put in a partial reference dataset. Subsequently, the capsule with radionuclides 8 is inserted into another of the holes of the Plexiglas plate and the above-described procedure is repeated. In order to determine a reference dataset of this type, various radionuclides 8 ($^{99m}$Tc, $^{131}$I, $^{18}$F, each with 1 MBq) are used according to the embodiment example. A separate reference dataset is determined for each radionuclide 8.

The third system is formed by the sample body 19 (see FIG. 3), for example, a cow liver. A capsule with a radionuclide 8 ($^{99m}$Tc solution, 1 MBq) is inserted into the latter. The method according to the invention makes it possible to check the match between a respective location of origin 9 in a tissue and the localization of this location of origin 9 by means of the third system.

Figure 2:
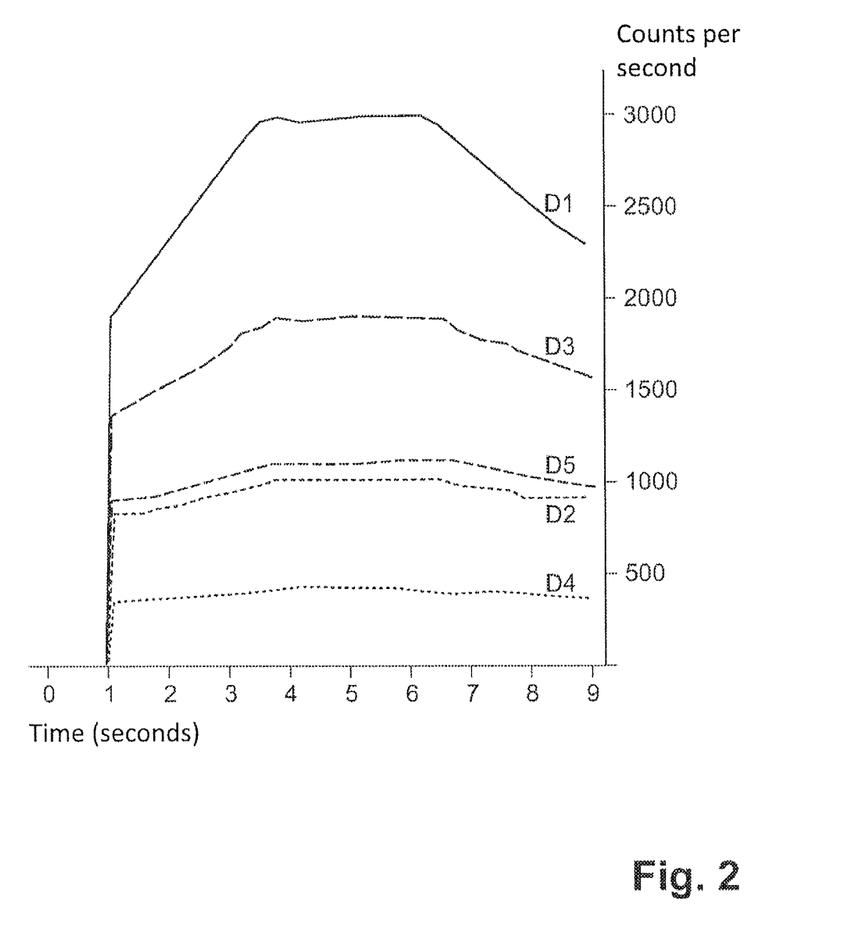
FIG. 2 is a schematic diagram of detection curves of five radiation detectors.

In FIG. 2, measurement values are plotted over time (seconds) schematically as first to fifth detection curves D1 to D5 in the form of sliding averages of the counting events per second (cps). Therefore, the counting events are associated with measurement times. The first detection curve D1 shows the counting events detected for the first radiation detector 2.1, the second detection curve D2 shows the counting events detected for the second radiation detector 2.2, up to the fifth detection curve D5 which shows the counting events detected for the fifth radiation detector 2.5.

The shapes of the individual first to fifth detection curves D1 to D5 show that the differences in the counting events vary in intensity to a greater or lesser extent over the duration of the measurements (in this case, about 8 seconds) through the individual first to fifth radiation detectors 2.1 to 2.5. To determine specific data, the averages of the measurement times of four to six seconds are used as measurement values and are related to one another. The results of these relationships are stored as specific data of the location of origin 9 in the partial reference dataset so as to be associated as partial reference dataset with the location of origin 9 and with the measurement time.

Figure 3:
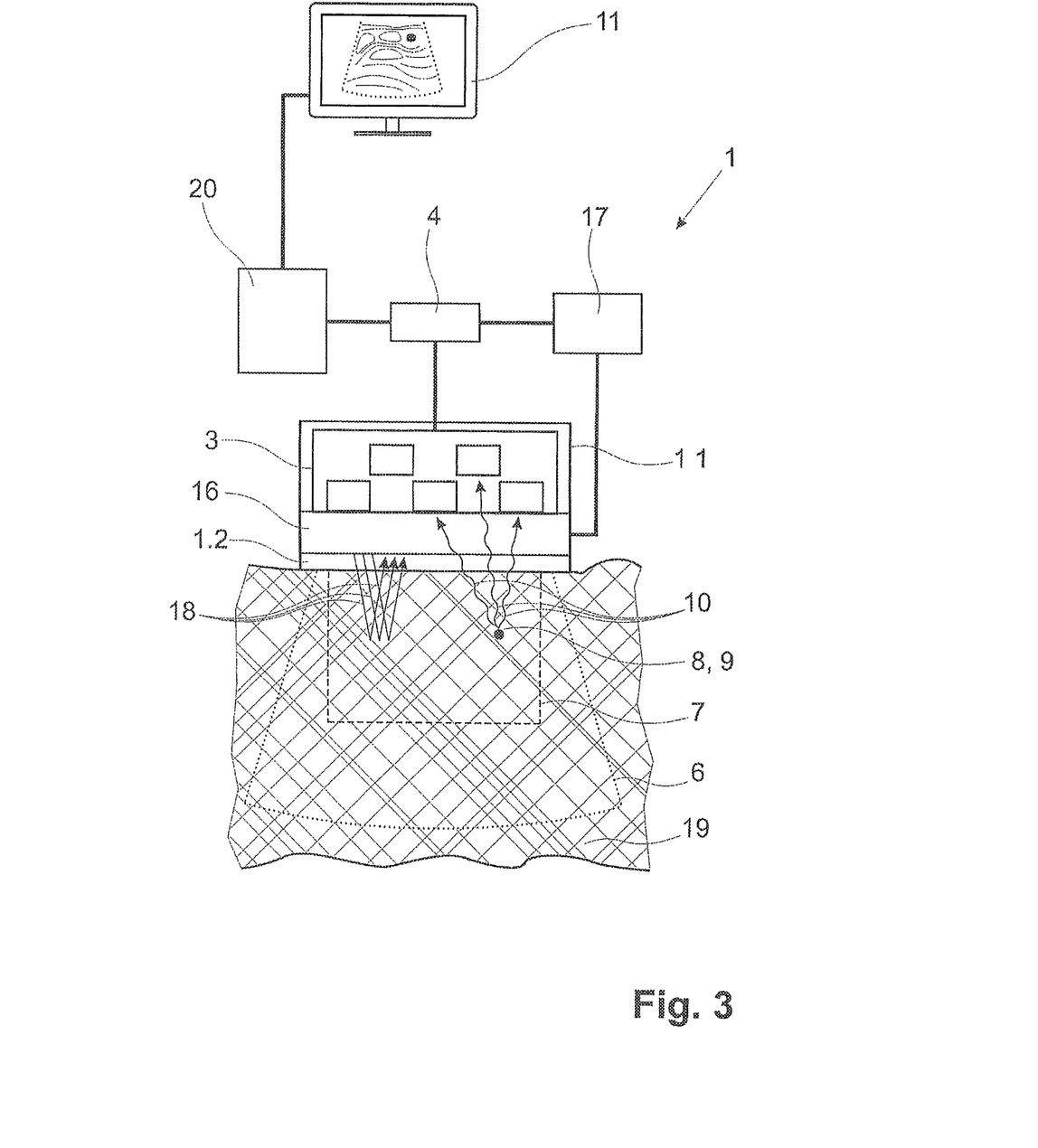
FIG. 3 is a first embodiment example of a measuring device according to the invention with an array of radiation detectors and an ultrasound probe arranged in a measuring head in front of the array.

In a further construction of the measuring device 1 according to the invention shown in FIG. 3, when an ultrasound probe 16 is arranged in addition to the array 3 and ultrasound signals 18 (represented by straight arrows) are also detected at the same time as the radiation signals 10, hybrid images can be generated and displayed based on the two types of signals. The intensities of the radiation signals 10 are displayed so as to be associated with their locations of origin 9 in that they are imaged in color and/or by corresponding brightness values corresponding to the intensity. At the same time, the imaging of the locations of origin 9 is superimposed on an image of the ultrasound signals 18 correctly with respect to location and position, and the contrast and brightness value are selected such that the images can be visually perceived simultaneously based on the radiation signals 10 and ultrasound signals 18. An imaging which is anatomically correct with respect to location and position is carried out by an image processing unit 20 by means of which there is a fusion of the provided measurement values of the radiation signals 10 and the findings based on the ultrasound signals 18 in the measurement zone 7.

In the first embodiment example of a measuring device 1 according to the invention shown in FIG. 3, the ultrasound probe 16 is arranged in the measuring head 1.1 in front of an array 3 in a space-saving manner.

A cow liver is provided as sample body 19 in the detection zone 6 as a third system. A capsule (only suggested in the drawing) with a $^{99m}$Tc solution (1 MBq) is inserted in the sample body 19 at a location with known coordinates. In this case, the degree of matching between the image of the locations of origin 9 of the radiation signals 10 and their intensity and the image of the tissue structures (findings) detected by the ultrasound signals 18 can be checked by means of the third system.

Figure 4:
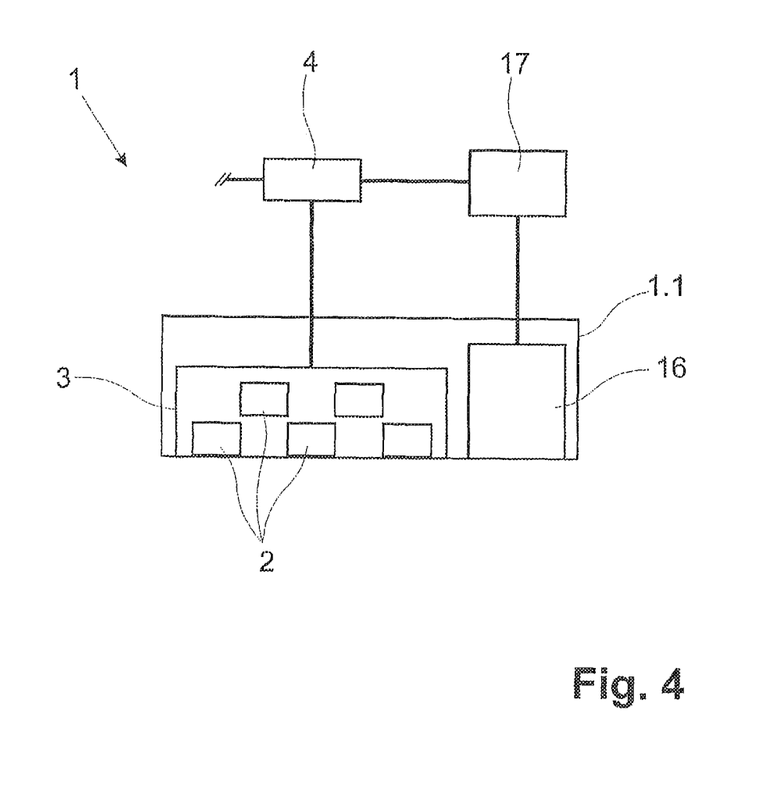
FIG. 4 is a second embodiment example of a measuring device according to the invention with an array of radiation detectors and an ultrasound probe arranged in a measuring head next to the array.

A second embodiment example of a measuring device 1 according to the invention with an array 3 of radiation detectors 2 and an ultrasound probe 16 arranged next to the array 3 in a measuring head 1.1 is shown in FIG. 4. For the sake of simplicity, some elements of the measuring device 1 such as the radiation detectors 2, array 3 and ultrasound probe 16 are shown only schematically. The ultrasound probe 16 is integrated in the measuring head 1.1 and is connected to an ultrasound device 17 in a known manner. This ultrasound device 17 is signally connected to the evaluating unit 4.

Figure 5:
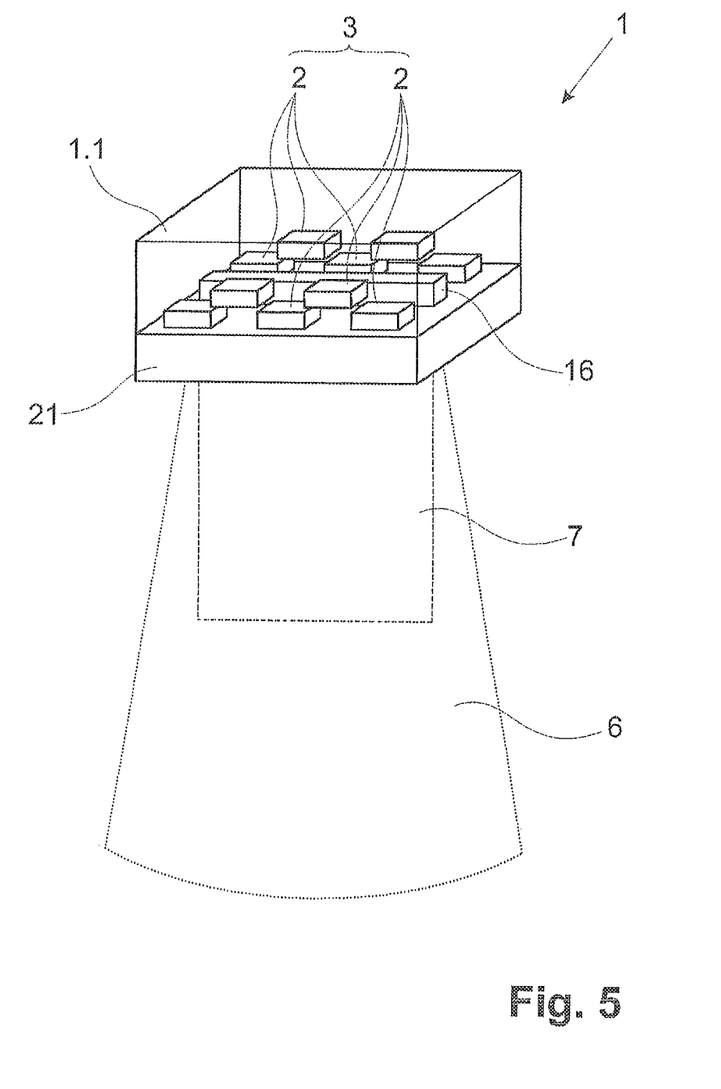
FIG. 5 is a third embodiment example of a measuring device according to the invention with an array of radiation detectors and an ultrasound probe arranged in a measuring head in the array.

In further embodiments of the measuring device 1 according to the invention, the ultrasound probe 16 can also be arranged in the array 3 of radiation detectors 2 as is shown in FIG. 5 as third embodiment example of the measuring device 1 according to the invention. The drawing shows the measuring head 1.1 with an array 3 of radiation detectors 2 (only ten of which are shown) and an ultrasound probe 16 which is arranged between two rows of radiation detectors 2 of the array 3. A collimator 21 which operates to limit the detection zone 6 of the array 3 laterally and sharply reduces passage of radiation signals 10 (not shown, see FIG. 1) not originating from the measurement zone 7 to the radiation detectors 2 is additionally arranged at the measuring head 1.1.

In further embodiments of the measuring device 1 according to the invention, other quantities of radiation detectors 2 can be arranged in arrays 3 of other configurations.

While the invention has been illustrated and described in connection with currently preferred embodiments shown and described in detail, it is not intended to be limited to the details shown since various modifications and structural changes may be made without departing in any way from the spirit of the present invention. The embodiments were chosen and described in order to best explain the principles of the invention and practical application to thereby enable a person skilled in the art to best utilize the invention and various embodiments with various modifications as are suited to the particular use contemplated.

LIST OF REFERENCE CHARACTERS 1 measuring device
1.1 measuring head
1.2 entrance window
2 radiation detector
2.1 first radiation detector
2.2 second radiation detector
2.3 third radiation detector
2.4 fourth radiation detector
2.5 fifth radiation detector
3 array (of radiation detectors 2)
4 evaluating unit
5 workstation
6 detection zone
7 measurement zone 8 radionuclide
9 location of origin
10 radiation signal
11 display
12 preamplifier
13 modulator
14 discriminator
15 counter card
16 ultrasound probe
17 ultrasound device
18 ultrasound signal
19 sample body
20 image processing unit
21 collimator
D1 first detection curve
D2 second detection curve
D3 third detection curve
D4 fourth detection curve
D5 fifth detection curve

What is claimed is:

1. A method for determining locations of origin of radiation signals of decaying radionuclides in a measurement zone being a section of a layer extending in an X-Z plane of a Cartesian coordinate system, comprising: arranging a quantity of radiation detectors for receiving radiation signals from the measurement zone and for providing measurement values based on received radiation signals in a known relative spatial arrangement relative to one another and relative to the measurement zone in such a way that they have different distances from the measurement zone, wherein each of the radiation detectors has a different geometric efficiency with respect to the detection of radiation signals which originate from different locations of origin inside the measurement zone; detecting radiation signals from the measurement zone at a measurement time by means of each individual radiation detector of the quantity of radiation detectors and, based on the detected radiation signals, providing measurement values so as to be associated with the measurement time; determining the locations of origin of the radiation signals by taking into account the measurement values of all of the radiation detectors and the known relative positional relationships of the radiation detectors relative to one another and relative to the measurement zone by comparing with a reference dataset associated with the measurement zone, wherein the reference dataset is made up of a quantity of partial reference datasets which are associated in each instance with a location of origin, and every partial reference dataset is formed by specific data of one of the locations of origin in each instance, and the specific data are formed by relationships of measurement values of the radiation detectors with respect to one another.

2. The method according to claim 1, wherein the locations of origin of the detected radiation signals are determined at a measurement time and are provided for a graphic depiction of the measurement zone with the locations of origin.

3. The method according to claim 2, further comprising detecting ultrasound signals from the measurement zone at the measurement time and providing said ultrasound signals as ultrasound measurement values associated with the measurement time for a graphic depiction of the measurement zone, and displaying the locations of origin and the ultrasound measurement values in a graphic display simultaneously and correctly with respect to location and position.

4. The method according to claim 1, wherein the radiation detectors are arranged without a collimator upstream of the radiation detectors on the reception side.

5. A measuring device for simultaneously detecting radiation events of decaying radionuclides in a measurement zone being a section of a layer extending in an X-Z plane of a Cartesian coordinate system, comprising: a measuring head having an entrance window, in which measuring head a quantity of radiation detectors having different distances from the entrance window provided in an arrray at a measurement position, said radiation detectors configured to receive radiation signals from the measurement zone and to provide measurement values based on received radiation signals; each of the radiation detectors having a different geometric efficiency with respect to the detection of measurement values of radiation signals which originate from different locations of origin inside the measurement zone; an evaluating unit for evaluating the radiation signals and for determining the locations of origin, said evaluating unit being configured in such a way that the locations of origin of the detected radiation signals can be determined from a quantity of measurement values which were detected at only one of the measurement positions of the measuring head and which are compared with data of a reference dataset which is associated with the measurement zone, said reference dataset being made up of a quantity of partial reference datasets, each partial reference dataset being formed by specific data of one of the locations of origin in each instance, and the specific data of each partial reference dataset being formed by relationships of measurement values of the radiation detectors relative to one another.

6. The measuring device according to claim 5, wherein the radiation detectors are arranged alternatingly in at least one X-Z plane perpendicular to the entrance window, wherein front radiation detectors are arranged directly at the entrance window and rear radiation detectors are arranged farther away from the entrance window, and thus from the measurement zone.

7. The measuring device according to claim 6, further comprising at least one ultrasound probe arranged in the measuring head for transmitting and receiving ultrasound signals from the measurement zone.

8. The measuring device according to claim 5, wherein the measuring device is constructed as a measuring device without a collimator.

9. The measuring device according to claim 5, wherein the measuring head is a portable device and is configured to be held and guided by a hand of a user.

10. The measuring device according to claim 7, further comprising at least one ultrasound probe arranged in the array of radiation detectors.

11. The measuring device according to claim 7, further comprising at least one ultrasound probe arranged next to the array of radiation detectors.

12. The measuring device according to claim 7, wherein said array of radiation detectors is arranged behind the at least one ultrasound probe so that the radiation signals pass through regions of the ultrasound probe before they can be detected by the radiation detectors.

13. The measuring device according to claim 5, further comprising at least one ultrasound probe arranged in the measuring head for transmitting and receiving ultrasound signals from the measurement zone.

* * * * *